United States Patent [19]

Yamane et al.

[11] Patent Number: 4,759,072
[45] Date of Patent: Jul. 19, 1988

[54] METHOD AND APPARATUS FOR DETECTION OF SURFACE DEFECTS OF HOT METAL BODY

[75] Inventors: Hirosato Yamane, Kurashiki; Hideyuki Hanafusa, Takamatsu, both of Japan

[73] Assignees: Kawasaki Steel Corp., Hyogo; Futec, Incorporated, Kagawa, both of Japan

[21] Appl. No.: 48,477

[22] Filed: May 6, 1987

Related U.S. Application Data

[63] Continuation of Ser. No. 684,243, Dec. 20, 1984, abandoned.

[30] Foreign Application Priority Data

Feb. 28, 1984 [JP] Japan ................................. 59-35232
Feb. 28, 1984 [JP] Japan ................................. 59-35233

[51] Int. Cl.⁴ .............................................. G06K 9/00
[52] U.S. Cl. .......................................... 382/8; 356/51; 356/237; 358/101; 358/106; 358/113; 250/330; 250/578
[58] Field of Search ................... 250/330, 342, 358.1, 250/359.1, 578; 356/51, 72, 237; 358/93, 101, 106, 107, 113; 382/8, 17, 22, 54

[56] References Cited

U.S. PATENT DOCUMENTS

| | | | |
|---|---|---|---|
| 3,727,054 | 4/1973 | Herrick | 250/358.1 |
| 3,748,471 | 7/1973 | Ross et al. | 358/113 |
| 4,118,732 | 10/1978 | Ichijima et al. | 358/106 |
| 4,319,270 | 3/1982 | Kimura et al. | 358/106 |
| 4,481,664 | 11/1984 | Linger et al. | 382/8 |
| 4,608,599 | 8/1986 | Kanek et al. | 358/113 |

FOREIGN PATENT DOCUMENTS 7704807  9/1978  France .
131192   of 1973  Japan .

OTHER PUBLICATIONS

I.S.A. Transactions, vol. 22, No. 3, 1983, pp. 59–69, ISA, Research Triangle Park, NC, US; E. T. Tromborg et al.: "Automated Inspection of Hot Steel Slabs", p. 67.

Primary Examiner—Leo H. Boudreau
Assistant Examiner—Jose L. Couso
Attorney, Agent, or Firm—Austin R. Miller

[57] ABSTRACT

In detecting surface defects of a hot metal body, e.g. hot-rolled steel sheet, by using a first video signal derived from radiation spontaneously radiated from a target area of the hot metal surface and a second video signal derived from external light projected on and reflected from the same target area of the hot metal surface, the rate of false detection by the influence of noise signals attributed to metal oxide present on the hot metal surface is greatly reduced by converting the first and second video signals respectively into first and second binary signals, synchronously feeding the first and second binary signals to an AND circuit and detecting the locations of such defects based on the output of the AND circuit. Preferably near-infrared region of the radiation is used in producing the first video signal and visible light as the external light.

13 Claims, 7 Drawing Sheets

METHOD AND APPARATUS FOR DETECTION OF SURFACE DEFECTS OF HOT METAL BODY

This application is a continuation of application Ser. No. 684,243, filed Dec. 20, 1984, now abandoned.

BACKGROUND OF THE INVENTION

This invention relates to a method of detecting surface defects of a hot metal body by using radiation emitted by the hot metal body and external light projected on and reflected by the same body, and to an apparatus for performing the surface defect detection method.

Conventional optical or televisional inspection methods for the detection of surface defects of a hot metal body, such as hot-rolled steel sheet, include the so-called passive method in which the surface defects are detected by analyzing a video signal derived from radiation such as infrared radiation emitted by the hot metal and the so-called active method in which external light is projected on the hot metal surface to produce a video signal from the reflected light.

In general hot metal surface defects attributed to material abnormality such as scabbing, scaling or brick inclusion are relatively easy to detect by the aforementioned passive method, but the surface defects classified as geometric abnormality such as simple dents are rather difficult to accurately detect by the same method because the difference in temperature between the defective region and the normal region of the hot metal surface is so small that an expected defect-indicating signal cannot easily be discriminated from noise signals. In the case of the active method it is relatively easy to detect the surface defects of the geometric abnormality type, but it is difficult to accurately detect the surface defects attributed to material abnormality by this method because in this case signals indicative of such surface defects cannot easily be discriminated from noise signals.

Thus, the passive method and the active method each have merits and demerits, and either of these methods is not truly suitable for accurate detection of surface defects of every type because the rate of false detection becomes considerably high as to surface defects of a specific type. The obstructive noise signals are mostly attributed to metal oxide that is inevitably formed on the hot metal surface to be inspected.

Japanese patent application provisional publication No. 49-131192 (1973) proposes to jointly employ the passive method and the active method with a view to detecting the surface defects of one type by using self-emitted light and the surface defects of other type by using the reflected light. However, also in this case noise signals offer considerable obstruction to accurate detection of surface defects of every type, partly because the reflected light is always received together with the self-emitted light.

In the above described conventional surface defect detection methods it is a common practice to perform a descaling treatment prior to the inspection for surface defects to thereby reduce noise signals at the stage of producing a video signal. However, even though such a pretreatment is performed it is difficult to accomplish complete removal of scale from the hot metal surface, and accordingly the problem of high rate of false detection remains unsolved.

SUMMARY OF THE INVENTION

It is an object of the present invention to provide an improved method of detecting surface defects of a hot metal body such as hot-rolled steel sheet, in which method the influence of noise signals is practically eliminated and by which method the rate of false detection can greatly be reduced without increasing the rate of undetected defects.

It is another object of the invention to provide an apparatus for performing the surface defect detection method according to the invention.

This invention provides a method of detecting surface defects of a hot metal body, the method comprising the steps of producing a first video signal by optical to electrical conversion of a selected region of radiation spontaneously radiated from a target area of a surface of the hot metal body, producing a second video signal by optical to electrical conversion of external light projected on and reflected from the target area of the hot metal surface, the external light being not interferential with the selected region of the aforementioned radiation, converting the first and second video signals respectively into first and second binary signals each of which assumes a logical "1" state when it implies the presence of a surface defect in the target area of the hot metal surface, making a logical product of the first and second binary signals in a synchronous state to thereby produce a third binary signal, and making a judgment as to the presence or absence of any surface defect in the target area of the hot metal surface.

As the basis of this invention, we have discovered an important fact about a difference between a video signal produced by the passive method described hereinbefore and another video signal produced by the active method also described hereinbefore. If there is a surface defect in a target area of the hot metal surface inspected by both the passive and active methods, a defect-indicating signal appears at a certain position on the scanning line of the video signal produced by the passive method, and a defect-indicating signal appears also at the exactly corresponding position on the scanning line of the video signal produced by the active method, though the two defect-indicating signals are different in amplitude. In contrast, noise signals attributed to metal oxide on the hot metal surface appear at some positions on the scanning lines of one video signal and at clearly different positions on the scanning lines of the other video signal.

In the method according to the invention, the first video signal derived from the self-emitted light and the second video signal derived from the reflected light are converted individually into two-valued or binary signals. The thus produced first and second binary signals both contain noise signals attributed to metal oxide on the hot metal surface. However, the noise signals are entirely eliminated by making logical products of the first and second binary signals while they are in a synchronous state, because noise signals contained in the first binary signal do not appear simultaneously with any noise signal contained in the second video signal. Consequently the third binary signal obtained by the logical multiplying operation is free of noise signals. If the third binary signal assumes a logical "1" state, that is certainly attributed to the presence of a surface defect in the inspected area of the hot metal surface.

By using the method of the invention the rate of false detection can remarkably be reduced even when the descaling pretreatment is omitted, because noise signals attributed to metal oxide or scale are filtered out in the above explained manner. Furthermore, it is possible to set the threshold in producing the binary signals at a relatively low level without causing significant increase in the rate of false detection, and therefore the rate of undetected defects is also reduced. In the case of using either of the conventional passive method and active method, the rate of false detection is usually 200–900% based upon the detections of five defects and the rate of undetected defects is usually about 10%. By using the method of the invention, the rate of false detection, defined as the proportion of the sum of true defect detection and false detection to the number of true defects, can be reduced to about 100% and the rate of undetected defects to about 5%. This invention is applicable to the inspection of various kinds of metals and alloys and is very suitable for detecting surface defects of hot-worked steels.

In producing a video signal from radiation spontaneously radiated from the hot metal surface, it is suitable to utilize the near-infrared region of the spectrum not shorter than 700 nm in wavelength. Then, it is suitable to use visible light of wavelengths ranging from about 400 nm to about 600 nm as the external light to be projected on and reflected by the hot metal surface.

An apparatus according to the invention for detection of surface defects of a hot metal body comprises first image pickup means for receiving a selected region of radiation spontaneously radiated from a target area of a surface of the hot metal body and converting the received radiation into a first video signal, projector means for projecting external light which is not interferential with the selected region of the aforementioned radiation on the target area of the hot metal surface, second image pickup means for receiving external light reflected from the target area of the hot metal surface and converting the received light into a second video signal, binary signal producing means for converting the first and second video signals respectively into first and second binary signals each of which assumes a logical "1" state when it implies the presence of a surface defect in the target area of the hot metal surface, an AND circuit to which the first and second binary signals are synchronously input, and judgment means for making a judgment as to the presence or absence of any surface defect in the target area of the hot metal surface based on the output of the AND circuit.

In this apparatus, the image pickup means and the projector means may be arranged so as to produce the first and second video signals simultaneously or, alternatively, with a time interval. In the latter case the apparatus includes a memory means and a synchronizing means to feed the first and second binary signals to the AND circuit synchronously. To produce the first and second video signals simultaneously, it is preferred to use an image pickup unit including an optical lens system to collect both the self-emitted light and the reflected external light, a light separating means for separating the light passed through the lens system into a near-infrared region and a visible region, a first image pickup device such as a linear array image sensor with a near-infrared transmitting filter attached thereto and a second image pickup device such as a linear array image sensor with a near-infrared absorbing filter attached thereto.

DETAILED DESCRIPTION OF THE INVENTION

In the method according to the invention the reflected light and the self-emitted light may be received either simultaneously or with a time interval. In either case the reflected light is always received together with the self-emitted light, and this becomes a cause of lowering of the signal to noise ratio (S/N ratio) in producing a video signal from the reflected light. To raise the S/N ratio it is required to use a selected region of the spectrum as the light to be reflected so that the self-emitted light may not be interferential with the reflected light, and the reflected light and the self-emitted light must be separated from each other prior to the optical to electrical conversion operation.

Figure 1:
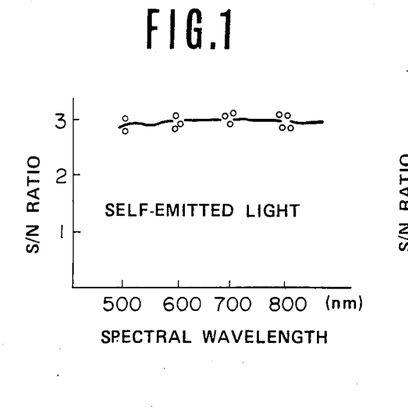
FIG. 1 is a graph showing the relationship between the spectral wavelength of light emitted by a hot metal body and the signal to noise ratio in producing a video signal by receiving only the emitted light.
Figure 2:
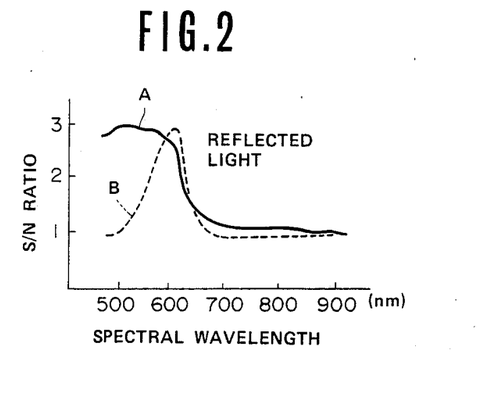
FIG. 2 is a graph showing the relationship between the spectral wavelength of light projected on and reflected by a hot metal body and the signal to noise ratio in producing a video signal by receiving the reflected light.
Figure 3:
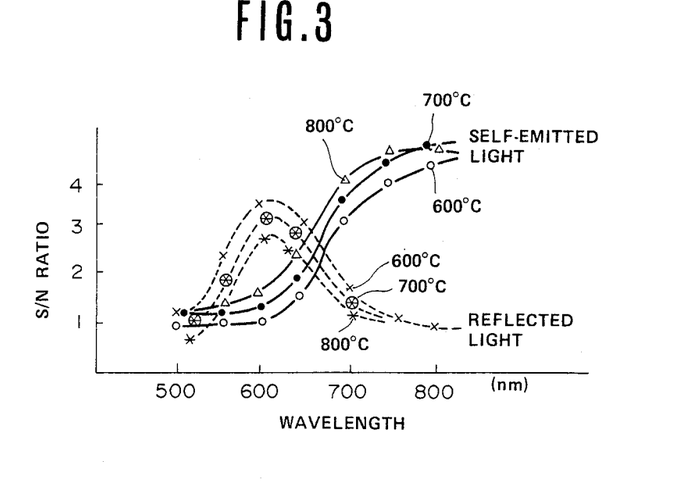
FIG. 3 is a graph showing the relationship between the spectral wavelength and the signal to noise ratio in producing video signals by receiving the self-emitted light and the reflected light simultaneously.

With respect to a steel sheet having a temperature of 600°–800° C., FIG. 1 shows the relationship between the spectral wavelength of the self-emitted light and the S/N ratio in producing a video signal by receiving the self-emitted light alone. In the case of producing a video signal by using external light projected on and reflected by the same steel sheet, the relationship between the spectral wavelength of the reflected light and the S/N ratio becomes as shown in FIG. 2. The curve A in solid line represents the use of an argon laser as the external light and the curve B in broken line the use of a mercury lamp with an infrared absorbing filter attached thereto as the light source. FIG. 3 shows similar relationships observed when the self-emitted light and the reflected light were simultaneously received. The external light source was a mercury lamp provided with an infrared absorbing filter. As can be seen in FIG. 1, the S/N ratio becomes fairly high over a relatively wide range of wavelength when receiving the self-emitted light independently. In contrast, FIG. 2 shows that when receiving the reflected light a high S/N ratio is attained only by using relatively short wavelengths within a narrow range. Furthermore, FIG. 3 shows that when receiving the self-emitted light and the reflected light simultaneously the S/N ratio in producing a video signal from the self-emitted light tends to considerably lower on the shorter side of the wavelength, whereas the relationship between the wavelength of the reflected light and the S/N ratio does not differ from the relationship shown in FIG. 2.

To avoid the obstructive influence of the reflected light on the self-emitted light at wavelengths shorter than 700 nm, it is preferable to utilize only near-infrared and infrared regions of the self-emitted radiation in converting it into a video signal to detect the surface defects of the hot metal body. As to the external light to be reflected, it is preferable to use a visible light of wavelengths ranging from 600 to 400 nm primarily because the inclusion of wavelengths greater than 600 nm will cause lowering of the S/N ratio in converting the reflected light into a video signal by the influence of the self-emitted radiation. Light of wavelengths shorter than 400 nm is inconvenient for practical use because ordinary optical glass as the material of the lens system in the image pickup device easily absorbs or reflects light of such short wavelengths so that it becomes difficult to utilize the light reflected by the hot metal body with an intensity high enough to keep the S/N ratio at a desirably high level. Of course it is unfavorable for industrial economy to use optical glass of special specification in the image pickup device merely for the purpose of using light of wavelengths shorter than 400 nm.

Figure 4:
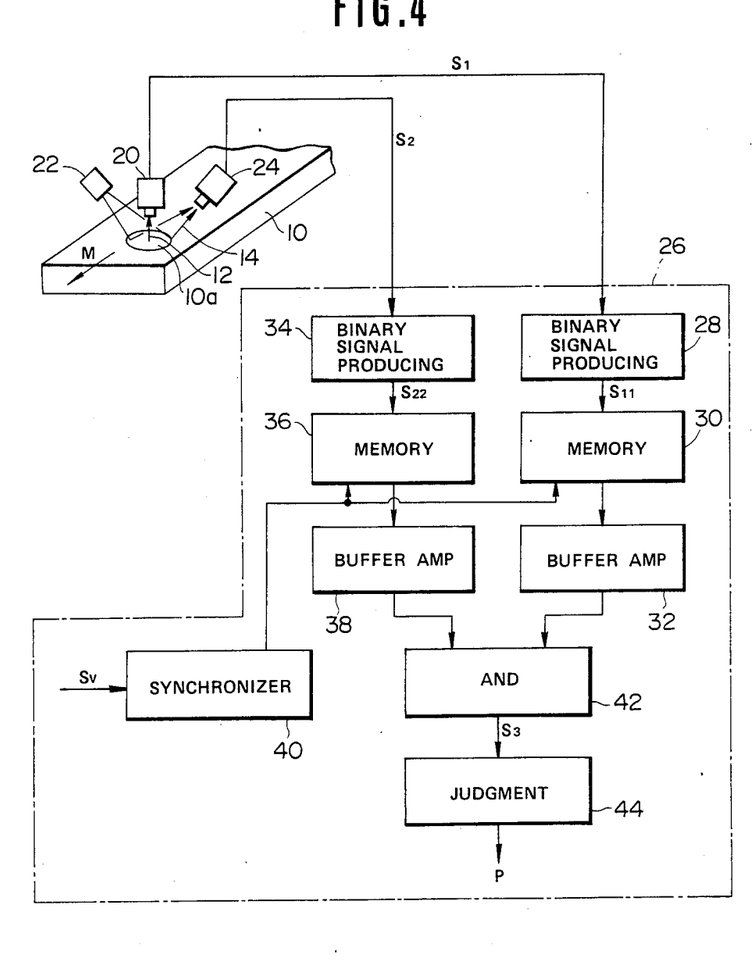
FIG. 4 is a diagrammatic illustration of an example of apparatus for performing a surface defect detecting method according to the invention.

The method according to the invention will be described in more detail with reference to FIG. 4. Numeral 10 indicates a hot metal sheet subject to inspection for surface defects while being transferred in the direction of arrow M. An image pickup device 20 is positioned right above a target area 10a of the surface of the hot metal sheet 10 to receive light 12 emitted by the hot metal sheet 10 and convert the received light into a video signal. The image pickup device 20 is provided with a near-infrared transmitting filter (not illustrated) which allows wavelengths greater than 700 nm to pass therethrough. A suitable example of this pickup device 20 is an infrared vidicon. A light projector 22, preferably an extra-high pressure mercury lamp, is arranged so as to project visible light of wavelengths of about 400–600 nm which is not interferential with the self-emitted light 12 on the target area 10a of the hot metal sheet 10, and an image pickup device 24 is arranged so as to receive light 14 reflected by the hot metal surface in the target area 10a to convert the received light 14 into a video signal. This image pickup device 24 may be of any type insofar as it is sensitive to a spectrum of wavelengths between 400 and 600 nm. For example, an ordinary camera tube for an industrial television system can be used with attachment of an infrared-absorbing filter to the lens system. Thus, the illustrated apparatus is so constructed as to receive the self-emitted light 12 and the reflected light 14 individually and simultaneously.

The image pickup device 20 produces a video signal $S_1$ from the self-emitted light 12 and the other image pickup device 24 another video signal $S_2$ from the reflected light 14. In a signal treating circuit 26 the signals $S_1$ and $S_2$ are treated in the following way. In a binary signal producing circuit 28 the video signal $S_1$ (which may or may not include noise) is converted into a binary signal $S_{11}$ which implies the existence of a surface defect in the target area 10a of the hot metal sheet 10 when it assumes its logical "1" state. In another binary signal producing circuit 34 the video signal $S_2$ (which may or may not include noise) is converted into a binary signal $S_{22}$ which implies the existence of a surface defect in the target area 10a of the hot metal sheet 10 when it assumes a logical "1" state. The output terminal of the binary signal producing circuit 28 is connected to an input terminal of an AND circuit 42 via a memory 30 and a buffer amplifier 32. Similarly the circuit 34 is connected to another input terminal of the AND circuit 42 via a memory 36 and buffer amplifier 38. The memories 30, 36 are controlled by a synchronizing circuit 40 to which a signal $S_y$ representing the rate of transfer of the hot metal sheet 10 is supplied. The output terminal of the AND circuit 42 (which includes little or no noise) is connected to a judgment circuit 44.

Figure 5:
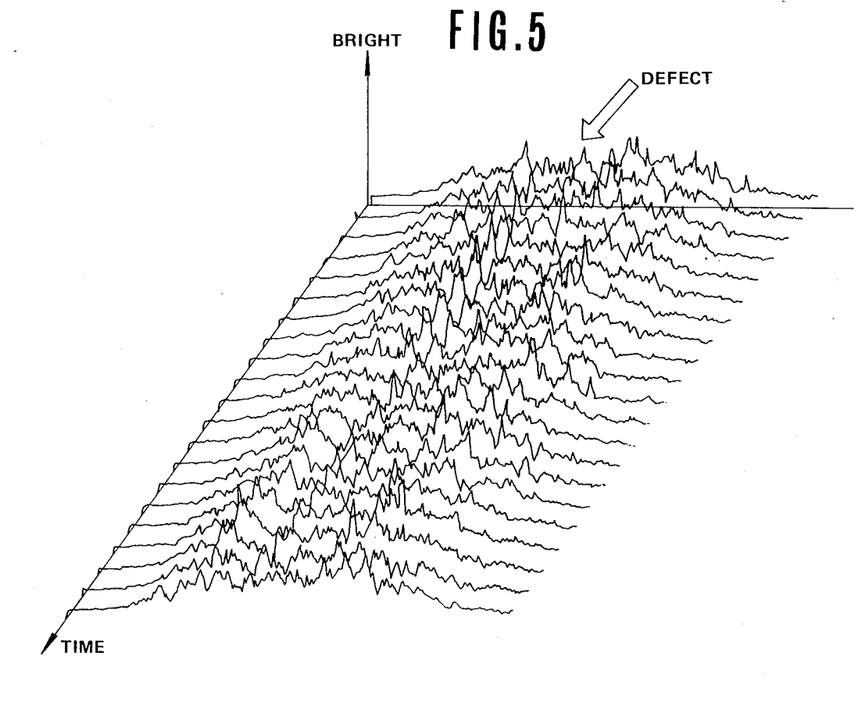
FIG. 5 shows the video signal derived from the self-emitted light on scanning lines.
Figure 6:
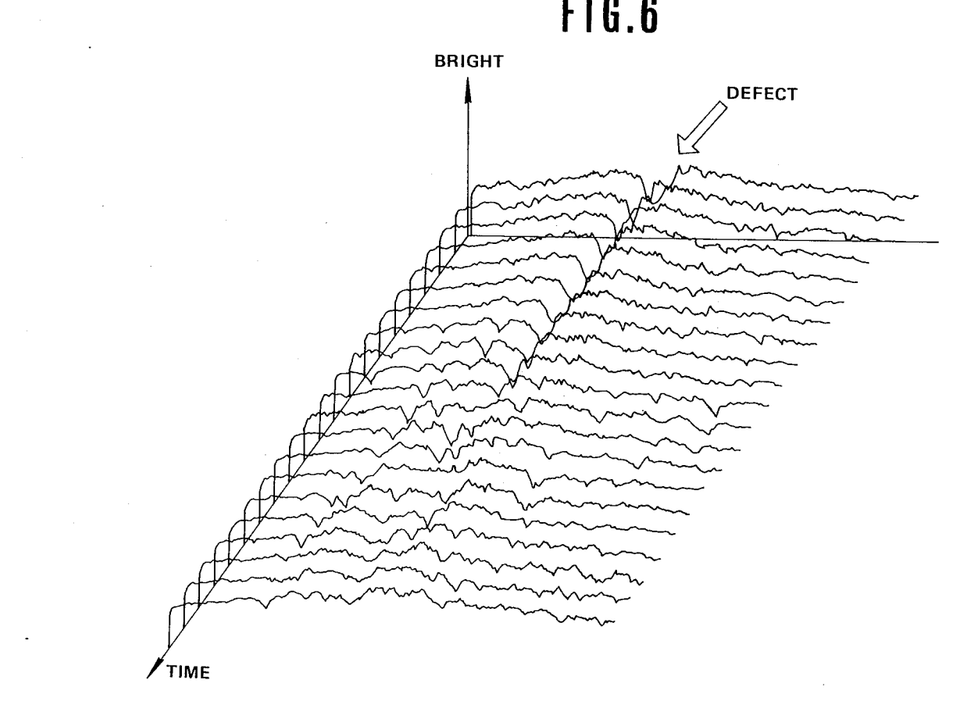
FIG. 6 shows the video signal derived from the reflected light on scanning lines.

FIG. 6 is an explanatory illustration of the video signal $S_2$ derived from the reflected light 14 on an excerpt portion of the scanning lines. FIG. 5 is a similar illustration of the video signal $S_1$ derived from the self-emittd light 12 on an excerpt portion of the scanning lines. In the video signal $S_2$ a defective area of the hot metal surface appears as a relatively dark region, while the same defective area of the hot metal surface appears in the video signal $S_1$ as a relatively bright region.

Figure 7:
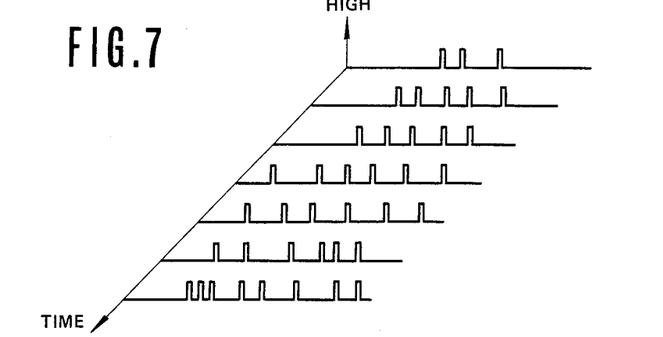
FIGS. 7 and 8 show defect-indicating binary signals obtained from the video signals of FIGS. 5 and 6, respectively.
Figure 8:
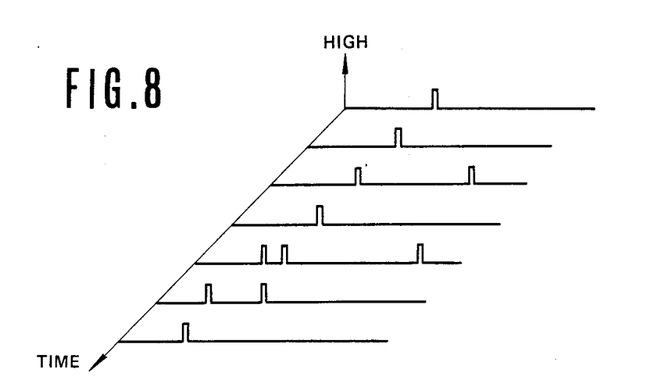

FIG. 7 shows the binary signal $S_{22}$ obtained by conversion of the video signal $S_2$ of FIG. 6 in the circuit 34 on the basis of a predetermined threshold level, and FIG. 8 shows the binary signal $S_{11}$ obtained by conversion of the signal $S_1$ of FIG. 5 in the circuit 28 on the basis of a predetermined threshold level. As can be seen in FIGS. 7 and 8, considerable noise signals are contained in the binary signals $S_{22}$ and $S_{11}$ and particularly in the former signal $S_{22}$. Therefore, false detection of surface defects is inevitable if a judgment is made from only one of these two sets of binary signals $S_{11}$ and $S_{22}$. In producing each of these binary signals $S_{11}$, $S_{22}$ it is conceivable to set the threshold at a relatively high level to thereby cut off the noise signals contained in the initial video signals $S_1$, $S_2$. Certainly this will be effective in decreasing the false detection rate, but it is also certain that such an improvement is accompanied by an increase in the rate of undetected defects and this is a matter of serious disadvantage. That is, the threshold must be set at a level low enough to minimize the rate of undetected defects and therefore the inclusion of noise signals in the binary signals $S_{11}$, $S_{12}$ is inevitable.

Figure 9:
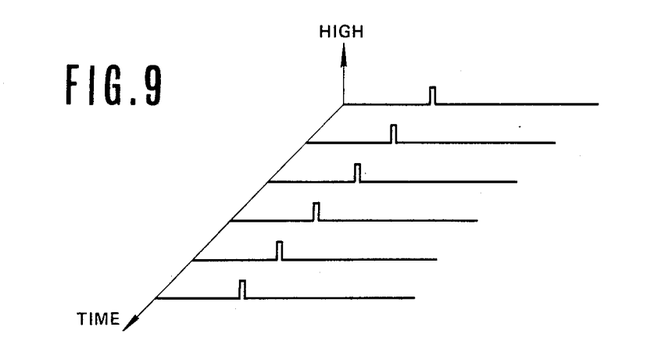
FIG. 9 shows a defect-indicating binary signal obtained by making a logical product of the binary signals of FIGS. 7 and 8.

In the method according to the invention the two sets of binary signals $S_{11}$ and $S_{22}$ are synchronized and input to the AND circuit 42, which provides a binary signal $S_3$ as the result of logical multiplication operation. If a surface defect exists in the target area 10a of the hot metal surface the binary signals $S_{11}$ and $S_{22}$ both assume the logical "1" state at the same positions on the scanning lines of the respective signals. Therefore, the binary signal $S_3$ as the output of the AND circuit 42 assumes a logical "1" state at the corresponding positions on the scanning lines, as shown in FIG. 9. The noise signals attributed to metal oxide present on the hot metal surface and contained in the initial video signals $S_1$, $S_2$ cause the binary signals $S_{11}$, $S_{22}$ to assume logical "1" state at some positions on the scanning lines as can be seen in FIGS. 7 and 8. However, none of the positions of the noise-indicating logical "1" state in the binary signals $S_{22}$ correspond to any position of any noise-indicating logical "1" state in the other binary signals $S_{11}$. Therefore, when the logical products of the two binary signals $S_{11}$ and $S_{22}$ are created the noise components of the respective signals $S_{11}$ and $S_{22}$ are entirely cut off to give a new binary signal $S_3$ which contains no noise component. This binary signal $S_3$ is fed into the judgment circuit 44 where a judgment is made, when the signal $S_3$ assumes the logical "1" state, whether a true defect exists in the target area 10a of the hot metal surface or not by examining the duration and continuity of the logical "1" state. The output P of this circuit 44 is used to indicate the detection of a surface defect in a desired manner.

When simultaneously receiving the self-emitted light 12 and the reflected light 14 to complete the inspection of the target area 10a of the hot metal sheet 10 by a single stage operation, the memories 30, 36 in the signal treating circuit 26 are unnecessary. However, in the present invention it is also possible to perform surveillance of the target area 10a by using the external light after or before surveillance of the same target area 10a by using the self-emitted light 12. For example, the projector 22 and the camera tube 24 may be set at a different location so as to survey the target area 10a after the transfer of the hot metal sheet 10 for a distance L. In that case the binary signal $S_{11}$ derived from the self-emitted light 12 is stored in the memory 30, and the synchronizing circuit 40 commands the memory 30 to output the stored binary signal $S_{11}$ after a time delay L/V, where V represents the rate of transfer of the hot metal sheet 10 indicated by the signal $S_v$, whereas the binary signal $S_{22}$ produced by using the projected and reflected light is immediately input to the AND circuit 42.

Figures 10, 11:
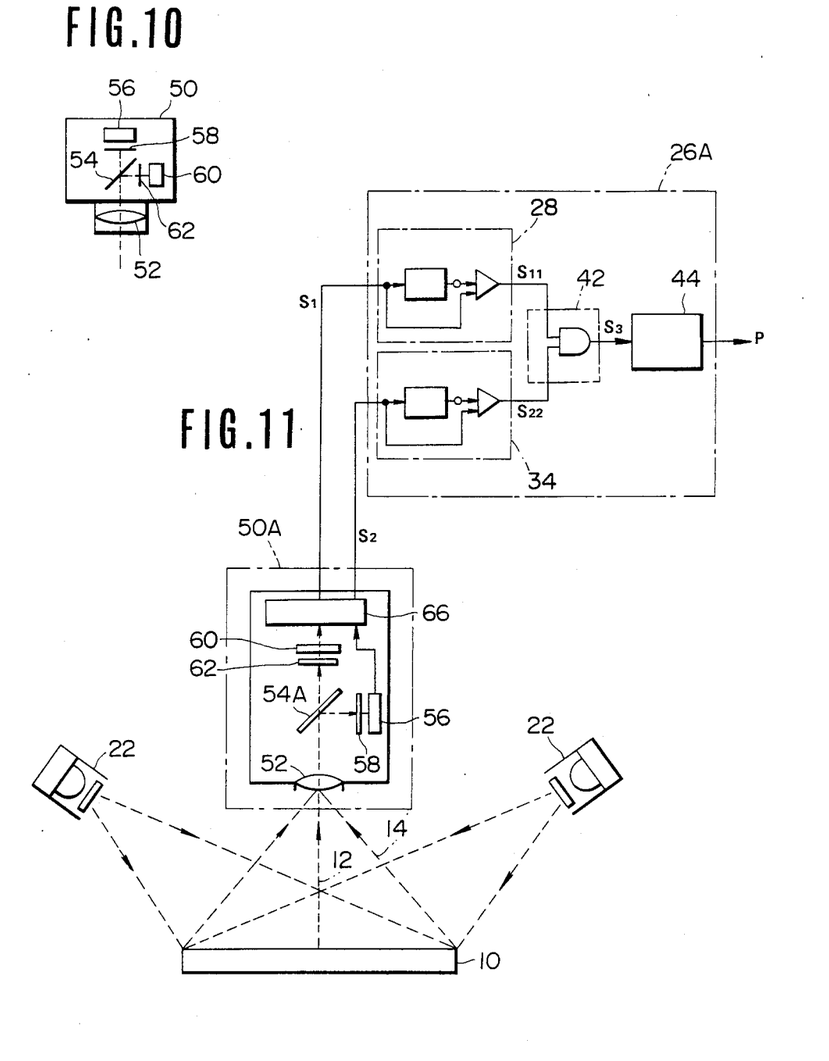
FIG. 10 is a schematic illustration of an image pickup device suitable for use in the present invention.
FIG. 11 is a diagrammatic illustration of a preferred example of surface defect detection apparatus according to the invention.

In the case of simultaneously receiving the self-emitted light 12 and the reflected light 14, the two image pickup devices 20 and 24 may be replaced by a single unit shown in FIG. 10. This image pickup unit 50 has an optical lens system 52, a first image pickup device 56 such as a linear array image sensor arranged axially in alignment with the lens 52, a cold-filter 54 disposed between the lens 50 and the image pickup device 56 at an angle of 45 degrees, an infrared absorbing filter 58 attached to the image pickup device 56, a second image pickup device 60 such as a linear array image sensor arranged normal to the axis of the lens 52 and directed toward the cold-filter 54 and an infrared transmitting filter 62 attached to the second image pickup device 60. The cold-filter 54 transmits visible light and reflects near-infrared spectrum. Accordingly the reflected light is received and converted into a video signal by the first image pickup device 56, while the self-emitted light is reflected by the cold-filter 54 toward the second image pickup device 60 which converts the received light into a video signal.

FIG. 11 shows a preferred embodiment of the apparatus according to the invention. This apparatus uses an image pickup unit 50A which is analogous to the unit 50 of FIG. 10 and positioned right above the hot metal body 10. Two projectors 22, preferably extra-high pressure mercury lamps, are arranged on the right and left sides of the image pickup unit 50A, respectively. Each projector 22 is provided with an infrared absorbing filter to project visible light of wavelengths of about 400-600 nm on the target area of the hot metal surface. When only one projector is used the projected light will possibly produce a shadow on the hot metal surface by reason of local peeling of metal oxide or scale. The use of the two projectors 22 is advantageous because such a shadow is eliminated by the light from the other projector. The apparatus of FIG. 11 includes a signal treating circuit 26A which is substantially similar to the circuit 26 in FIG. 4.

Figure 12:
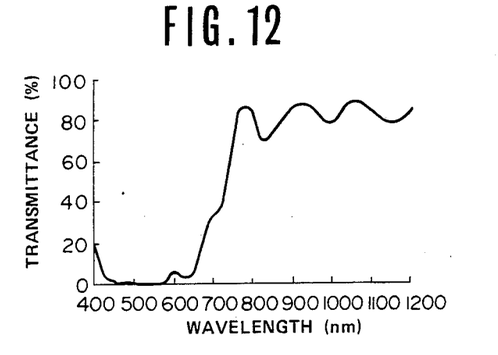
FIGS. 12, 13 and 14 are graphs showing the characteristics of the cold-mirror, infrared absorbing filter and infrared transmitting filter in the apparatus of FIG. 11, respectively.
Figure 13:
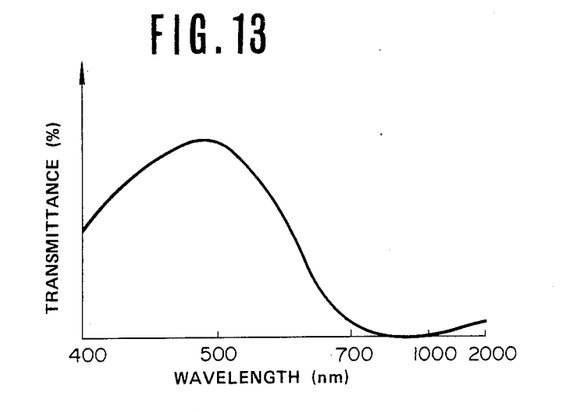
Figure 14:
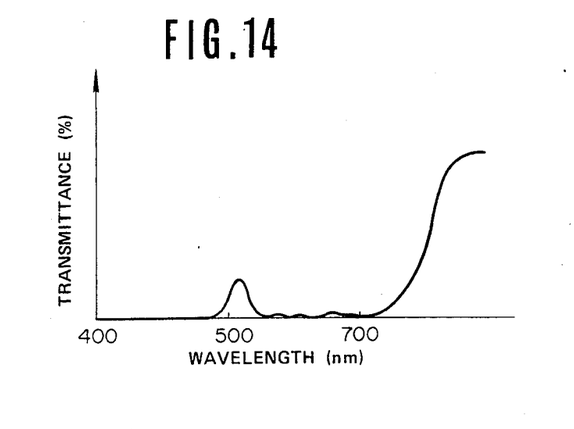

The image pickup unit 50A includes an optical lens system 52, a first linear array image sensor 56 with an infrared absorbing filter 58 attached thereto to receive the reflected light 14, a second linear array image sensor 60 with an infrared transmitting filter 62 attached thereto to receive the self-emitted light 12, a cold-mirror 54A employed as a light separating filter means, and a control circuit 66. The first linear array image sensor 56 is oriented normal to the axis of the lens 52, whereas the second linear array image sensor 60 is in alignment with the lens 52. The cold-mirror 54A is disposed between the lens 52 and the second linear array image sensor 60 at an angle of 45 degrees. This cold-mirror reflects visible spectrum below about 700 nm in wavelength and transmits near-infrared region of the spectrum greater than about 700 nm in wavelength. Typically, the characteristic of the cold-mirror 54A is as shown in FIG. 12. However, the light reflected by the cold-mirror 54A includes about 10-15% of near-infrared rays greater than 700 nm in wavelength. Therefore, the first image sensor 56 is provided with the infrared absorbing filter 58 of which the characteristic is typically as shown in FIG. 13. The light passed through the cold-mirror 54A includes near-ultraviolet rays and a red region of the spectrum ranging from about 600 to about 700 nm. Therefore, the second image sensor 60 is provided with the infrared transmitting filter 62 of which the characteristic is typically as shown in FIG. 14. The control circuit 66 controls the light-receiving and signal-producing operation of the respective image sensors 56, 60 and also serves as an interface in sending the video signals $S_1$ and $S_2$ from the unit 50A to the signal treating circuit 26A.

Alternative to the cold-mirror 54A in FIG. 11, a half-mirror or a cold-filter can be used. As described hereinbefore, the cold-filter 54 in FIG. 10 has a characteristic reverse to that of the cold-mirror 54A in FIG. 11. Therefore, the positions of the infrared absorbing filter 58 and the infrared transmitting filter 62 in FIG. 11 are interchanged in the unit 50 of FIG. 10.

What is claimed is:

1. A method of detecting surface defects of a hot metal body, comprising the steps of:
producing a first video signal by optical to electrical conversion of a selected region of radiation wavelength spontaneously radiated from a target area of a surface of the hot metal body by using a first image pickup means;
producing a second video signal by optical to electrical conversion of external light projected on and reflected at a selected wavelength region from said target area of the hot metal surface by using a second image pickup means, said external light wavelength region being not interferential with said selected region of said radiation;
converting said first and second video signals respectively into first and second binary signals each of which assumes a logical "1" state when it implies the presence of a surface defect in said target region of the hot metal surface;

making an AND treatment of said first and second binary signals in a synchronous state to thereby produce a third binary signal which indicates the presence of a defect on said hot metal body without the substantive presence of noise signals from said first and second video signals; and detecting the locations of such surface defect in said target area of the hot metal body based on said third binary signal.

2. A method according to claim 1, wherein said selected region of said radiation is a near-infrared region of the spectrum not shorter than 700 nm in wavelength, said external light being visible light, having a wavelength in the range from about 400 nm to about 600 nm.

3. A method according to claim 1, wherein said first and second video signals are produced simultaneously.

4. A method according to claim 1, wherein one of said first and second video signals is produced after producing the other.

5. A method according to claim 1, wherein said hot metal body is a hot-worked steel body.

6. An apparatus for detection of surface defects of a hot metal body, comprising:

first image pickup means for receiving a selected region of radiation spontaneously radiated at a selected wavelength region from a target area of a surface of the hot metal body and converting the received radiation into a first video signal;

projector means for projecting external light which is not interferential with said selected wavelength region of the radiation from said target area of the hot metal surface;

second image pickup means for receiving said external light reflected from said target area of the hot metal surface at a selected wavelength and converting the received light into a second video signal;

binary signal producing means for converting said first and second video signals respectively into simultaneously existing first and second binary signals each of which assumes a logical "1" state when it implies the presence of a surface defect in said target area of the hot metal surface;

an AND circuit to which said first and second binary signals are synchronously input to produce a third binary signal substantially free of noise signals contained in said first and second binary signals; and means of detecting the presence or absence of any surface defect in said target area of the hot metal surface based on the output of said AND circuit.

7. An apparatus according to claim 6, wherein said selected region of said radiation is in the near-infrared region of the spectrum not shorter than 700 nm in wavelength, said external light being visible light having a wavelength in the range from about 400 nm to about 600 nm.

8. An apparatus according to claim 7, wherein said projector means comprises a mercury lamp.

9. An apparatus according to claim 6, wherein said first and second image pickup means are so arranged as to produce one of said first and second video signals after producing the other video signal, the apparatus further comprising memory means for storing the binary signal produced from said one of said first and second video signals, and synchronizing means for controlling said memory means such that said first and second binary signals are synchronously input to said AND circuit.

10. An apparatus according to claim 7, further comprising an optical lens system arranged so as to collect both said radiation radiated from said target area and said external light reflected from said target area, a light separating means for separating light passed through said lens system into a first portion which is near-infrared region of the spectrum and a second portion which is visible region of the spectrum and directing said first and second portions toward said first and second image pickup means, respectively, a near-infrared transmitting filter which is provided to said first image pickup means and cuts off visible region of the spectrum and an infrared absorbing filter which is provided to said second image pickup means and transmits visible region of the spectrum.

11. An apparatus according to claim 10, wherein said light separating means comprises a cold-mirror.

12. An apparatus according to claim 10, wherein said light separating means comprises a cold-filter.

13. An apparatus according to claim 6, wherein each of said first and second image pickup means comprises a linear array image sensor.

* * * * *